United States Patent
Futahashi et al.

(10) Patent No.: US 11,090,240 B2
(45) Date of Patent: Aug. 17, 2021

(54) ULTRAVIOLET REFLECTING AGENT COMPOSITION AND WATER REPELLENT AGENT COMPOSITION

(71) Applicants: National Institute of Advanced Industrial Science and Technology, Tokyo (JP); Tokyo University of Agriculture, Tokyo (JP)

(72) Inventors: Ryo Futahashi, Tsukuba (JP); Migaku Kawaguchi, Tsukuba (JP); Takahiko Hariyama, Hamamatsu (JP); Yumi Yamahama, Hamamatsu (JP); Daisuke Ishii, Nagoya (JP); Shunsuke Yajima, Tokyo (JP); Ryouka Miki, Tokyo (JP); Naoki Mori, Kyoto (JP)

(73) Assignees: NATIONAL INSTITUTE OF ADVANCED INDUSTRIAL SCIENCE AND TECHNOLOGY, Tokyo (JP); TOKYO UNIVERSITY OF AGRICULTURE, Tokyo (JP)

(*) Notice: Subject to any disclaimer, the term of this patent is extended or adjusted under 35 U.S.C. 154(b) by 0 days.

(21) Appl. No.: 16/689,945

(22) Filed: Nov. 20, 2019

(65) Prior Publication Data

US 2020/0078280 A1    Mar. 12, 2020

Related U.S. Application Data

(63) Continuation of application No. PCT/JP2018/019559, filed on May 21, 2018.

(30) Foreign Application Priority Data

May 22, 2017 (JP) .................. 2017-100693

(51) Int. Cl.
A61K 8/34      (2006.01)
A61K 8/35      (2006.01)
(Continued)

(52) U.S. Cl.
CPC ............ *A61K 8/342* (2013.01); *A61K 8/35* (2013.01); *A61Q 17/04* (2013.01); *C09D 5/004* (2013.01); *C09K 3/18* (2013.01)

(58) Field of Classification Search
CPC .......... A61K 8/342; A61K 8/35; A61K 31/11; A61K 8/33; A61K 35/63; A61K 31/121;
(Continued)

(56) References Cited

U.S. PATENT DOCUMENTS

2015/0272841 A1* 10/2015 Fascina .............. A61K 8/37
424/59

FOREIGN PATENT DOCUMENTS

JP    H06145023 A    5/1994
JP    2011236182 A   11/2011

OTHER PUBLICATIONS

Hiroko et al. (JP2003113033A English Translation) (Year: 2003).*
(Continued)

*Primary Examiner* — Robert A Wax
*Assistant Examiner* — Quanglong N Truong
(74) *Attorney, Agent, or Firm* — Kilpatrick Townsend & Stockton LLP

(57) ABSTRACT

The present invention relates to an ultraviolet reflecting agent composition or a water repellent agent composition, which contains at least one compound selected from among 2-pentacosanone, 2-heptacosanone, 2-nonacosanone, tetracosanal, hexacosanal, octacosanal and triacontanal.

24 Claims, 11 Drawing Sheets

Specification includes a Sequence Listing.

(51) Int. Cl.
*A61Q 17/04* (2006.01)
*C09D 5/33* (2006.01)
*C09K 3/18* (2006.01)

(58) Field of Classification Search
CPC . A61Q 17/04; A61Q 5/00; A61Q 1/02; A61Q 17/00; A61Q 19/00; C09D 5/004; C09D 7/63; C09K 3/18; A61P 17/18; C08K 5/07
See application file for complete search history.

(56) References Cited

OTHER PUBLICATIONS

Wang, et al; Acute toxicity and biodistribution of different sized titanium dioxide particles etc; ScienceDirect—Toxicology Letters 168 (2007) 176-185.
Wang, et al; Acute toxicological impact of nano- and submicro-scald zinc oxide powder on healthy adult mice; J Nanopart Res (2008) 10:263-276.
Corbet, P.S.; Dragonflies, Behavior and Ecology of Odonata; Dragonflies and People—Cornell Univ. Press; (1999) p. 560.
Futahashi; Molecular mechanisms underlying color pattern diversity in dragonflies; AIST-RIKEN bioinformatics virtual joint laboratory; (Mar. 30, 2016).
Japan Patent Office; International Search Report of PCT/JP2018/019559; dated Aug. 14, 2018.

* cited by examiner

FIG. 11

ULTRAVIOLET REFLECTING AGENT COMPOSITION AND WATER REPELLENT AGENT COMPOSITION

CROSS-REFERENCE TO RELATED APPLICATIONS

The present application is a Continuation Application of International Application No. PCT/JP2018/019559, filed May 21, 2018, which claims priority to Japanese Patent Application No. 2017-100693, filed May 22, 2017, the disclosures of which are hereby incorporated by reference in their entireties for all purposes.

REFERENCE TO SUBMISSION OF A SEQUENCE LISTING AS A TEXT FILE

The Sequence Listing written in file SequenceLisitng_093803-005800US-1154200.txt created on Nov. 20, 2019, 2,920 bytes, machine format IBM-PC, MS-Windows operating system, is hereby incorporated by reference in its entirety for all purposes.

FIELD

The present invention relates to an ultraviolet reflecting agent composition and a water repellent composition. Further, the present invention relates to a method for protecting a subject from ultraviolet rays and a method for water-repellent treatment of a subject.

BACKGROUND

Excessive exposure to the ultraviolet rays in sunlight has negative effects such as the formation of blisters and erythema on the skin, and pigmentation. In addition, exposure to ultraviolet rays over a long period of time is known to promote aging of the skin, and cause blemishes, freckles, and wrinkles, and furthermore, skin cancer. Anti-ultraviolet agents are in demand to prevent the adverse effects of ultraviolet rays on the skin. For example, the possible use of a composition comprising a metal oxide having an ultraviolet reflecting effect, such as titanium oxide or zinc oxide in a cosmetic sunscreen composition has been reported (PTL 1). However, toxicity has been observed with the use of titanium oxide or zinc oxide (NPL 1 and 2).

In addition, there is a need in the cosmetics field for agents that can impart water repellence to subjects. For example, a water-repellent cosmetic comprising silicone oil, which can be used in cream and lotion as skin cosmetics, emulsion foundation and makeup base as makeup cosmetics, and hair cream and hair treatment as hair cosmetics, has been reported (PTL 2).

The white tailed skimmer dragonfly is the most commonly seen variety of dragonfly in Japan. It has been known for its use as a traditional medicine in the past (NPL 3). Therefore, the components of the white tailed skimmer dragonfly may be considered to be non-toxic and safe.

Immature white tailed skimmer dragonflies, both male and female, are straw-colored. As males mature, they change to bright blue and create their territory near the waterside in an area with strong sunlight. The body color of mature females does not change much, except that the ventral side of the abdomen become white. Aged individuals, both male and female, are strongly whitish on the whole. Such color changes are brought about by differences in the nanostructures of the body surface (NPL 4).

CITATION LIST

Patent Literature

[PTL 1] Japanese Unexamined Patent Publication (Kokai) No. 2011-236182.
[PTL 2] Japanese Unexamined Patent Publication (Kokai) No. 06-145023.

Non-Patent Literature

[NPL 1] Wang et al., 2007. Acute toxicity and biodistribution of different sized titanium dioxide particles in mice after oral administration. Toxicology Letters, 168(2): 176-185.
[NPL 2] Wang et al., 2008. Acute toxicological impact of nano- and submicro-scaled zinc oxide powder on healthy adult mice. Journal of Nanoparticle Research, 10(2): 263-276.
[NPL 3] Corbet, P. S., "Dragonflies, Behavior and Ecology of Odonata", 1999, Cornell University Press, p. 560.
[NPL 4] Futahashi, Ryo. "Molecular mechanisms underlying color pattern diversity in dragonflies", [online], Mar. 30, 2016. AIST-RIKEN Joint Seminar [Search Apr. 1, 2017], Internet, [URL: http://biodata.aist.riken.jp/seminar]

SUMMARY

Technical Problem

The object of the present invention is to provide a composition having ultraviolet reflecting effect and/or water repelling effect.

Solution to Problem

The present inventors discovered, surprisingly, that the mature male white tailed skimmer dragonfly is covered with wax, and is colored white by the structural color, and the wax reflects ultraviolet light. Furthermore, they discovered that specific long-chain aliphatic aldehydes and ketones, which are constituent components of the wax present on the surface of mature male dragonflies, have strong ultraviolet reflecting ability and high water repellence, thereby arriving at the present invention.

The present invention comprises the following [1] to [24].

[1]

A method for protecting a subject from ultraviolet rays comprising applying at least one compound selected from 2-pentacosanone, 2-heptacosanone, 2-nonacosanone, tetracosanal, hexacosanal, octacosanal, and triacontanal to the subject.

[2]

The method according to [1], wherein, when the compound is applied to a subject, the surface structure wherein the spectral reflectance for UV light with a wavelength 400 nm or less is not less than 30% is formed.

[3]

The method according to [1], wherein the compound is 2-pentacosanone.

[4]
The method according to [1], wherein the compound is in crystalline form having a structure formed by repeatedly dripping a solution of the compound onto a substrate.

[5]
The method according to [1], wherein the subject is an animal.

[6]
The method according to [1], wherein the subject is human skin.

[7]
The method according to [1], wherein the subject is a material selected from paper, metal, wood, glass, plastic, concrete or ceramic.

[8]
A method for water-repellent treatment of a subject comprising applying at least one compound selected from 2-pentacosanone, 2-heptacosanone, 2-nonacosanone, tetracosanal, hexacosanal, octacosanal, and triacontanal to the subject.

[9]
The method according to [8], wherein, when the compound is applied to a subject, the surface structure wherein the water contact angle is not less than 150° is formed.

[10]
The method according to [8], wherein the compound is 2-pentacosanone.

[11]
The method according to [8], wherein the compound is in crystalline form having a structure formed by repeatedly dripping a solution of the compound onto a substrate.

[12]
The method according to [8], wherein the subject is an animal.

[13]
The method according to [8], wherein the subject is human skin.

[14]
The method according to [8], wherein the subject is a material selected from paper, metal, wood, glass, plastic, concrete or ceramic.

[15]
A method of producing an ultraviolet reflecting agent composition comprising the step of repeatedly dripping a solution of at least one compound selected from 2-pentacosanone, 2-heptacosanone, 2-nonacosanone, tetracosanal, hexacosanal, octacosanal, and triacontanal onto a substrate to form a crystalline form thereof, wherein the ultraviolet reflecting agent comprises the crystalline form as an active agent.

[16]
The method according to [15], wherein, when the ultraviolet reflecting agent composition is applied to a subject, the surface structure wherein the spectral reflectance for UV light with a wavelength 400 nm or less is not less than 30% is formed.

[17]
The method according to [15], wherein the compound is 2-pentacosanone.

[18]
The method according to [15], wherein the ultraviolet reflecting agent composition is a cosmetic.

[19]
The method according to [15], wherein the ultraviolet reflecting agent composition is a paint.

[20]
A method of producing a water repellent composition comprising the step of repeatedly dripping a solution of at least one compound selected from 2-pentacosanone, 2-heptacosanone, 2-nonacosanone, tetracosanal, hexacosanal, octacosanal, and triacontana onto a substrate to form a crystalline form thereof, wherein the water repellent composition comprises the crystalline form as an active agent.

[21]
The method according to [20], wherein, when the water repellent composition is applied to a subject, the surface structure wherein the water contact angle is not less than 150° is formed.

[22]
The method according to [20], wherein the compound is 2-pentacosanone.

[Claim 23]
The method according [20], wherein the water repellent composition is a cosmetic.

[24]
The method according to [20], wherein the water repellent composition is a paint.

Advantageous Effects of Invention

According to the present invention, since an ultraviolet reflecting property can be imparted to an application subject of the composition of the present invention, and the application subject can be protected from ultraviolet light. Additionally, the composition of the present invention can impart water repellence to the application subject. The composition of the present invention can be used in fields such as cosmetics and paints.

BRIEF DESCRIPTION OF DRAWINGS

FIG. 11 shows the results of gene expression analysis of white tailed skimmer dragonflies.

DESCRIPTION OF EMBODIMENTS

Figure 1:
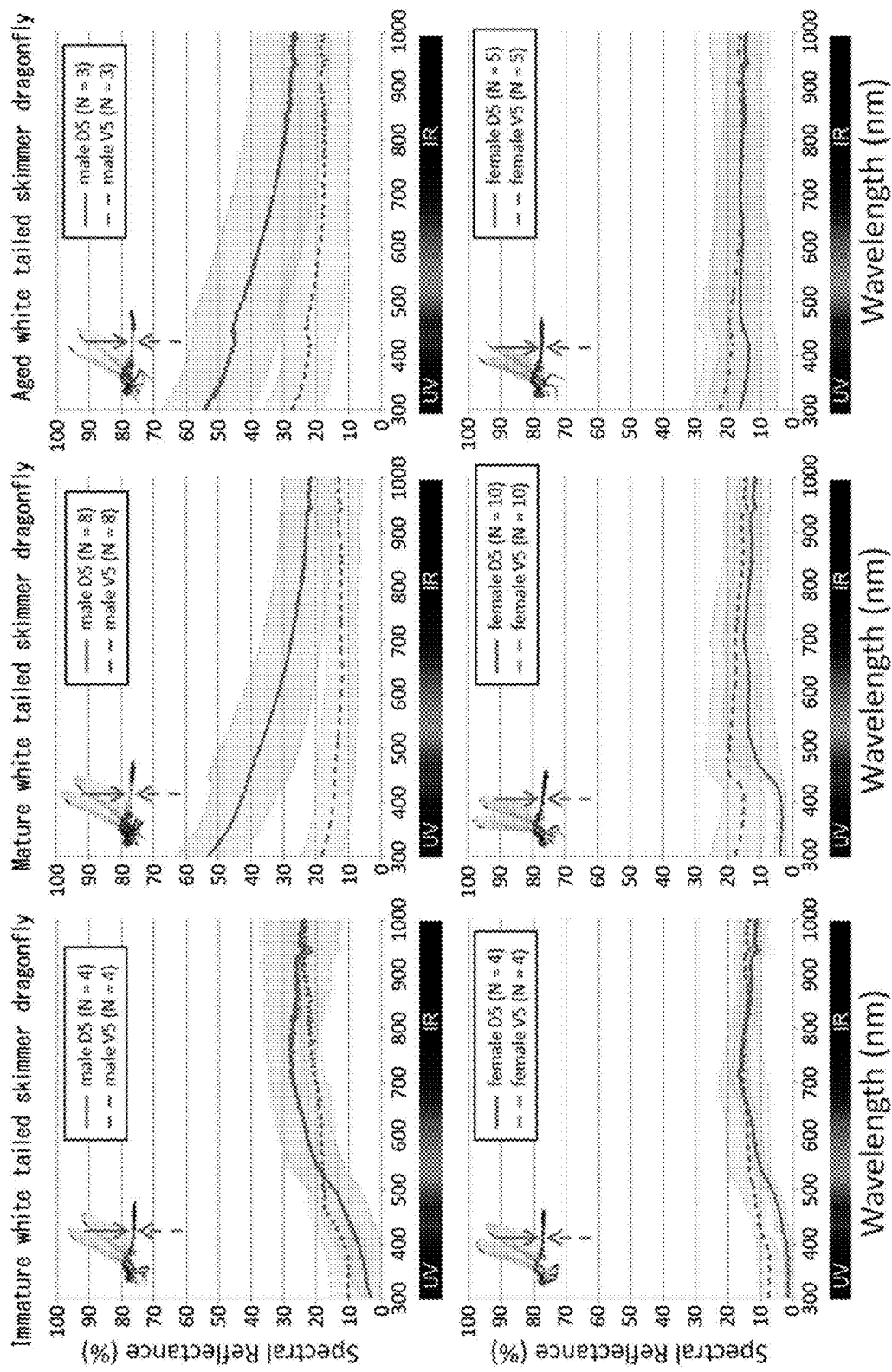
FIG. 1 shows spectral distributions (average value±SD (%)) of dorsal sides (D5) and ventral sides (V5) of the fifth segments of the abdomens of male and female white tailed skimmer dragonflies.

One aspect of the present invention provides an ultraviolet reflecting agent composition comprising at least one compound (hereinafter referred to as "active agent of the composition of the present invention") selected from 2-pentacosanone ($C_{25}H_{50}O$), 2-heptacosanone ($C_{27}H_{54}O$), 2-nonacosanone ($C_{29}H_{58}O$), tetracosanal ($C_{24}H_{48}O$), hexacosanal ($C_{26}H_{50}O$), octacosanal ($C_{28}H_{54}O$), and triacontanal ($C_{30}H_{60}O$). The aforementioned ultraviolet reflecting agent composition will hereinafter be referred to as "ultraviolet reflecting agent composition of the present invention."

In the present description, "ultraviolet reflecting agent composition" refers to a composition comprising a substance which functions as an ultraviolet light reflector, and is used to impart an ultraviolet reflecting property to an application subject of the composition, thereby protecting the application subject from ultraviolet light.

Another aspect of the present invention provides a water repellent composition comprising at least one compound selected from 2-pentacosanone, 2-heptacosanone, 2-nonacosanone, tetracosanal, hexacosanal, octacosanal, and triacontanal. The aforementioned water repellent composition will hereinafter be referred to as "water repellent composition of the present invention."

In the present description, "water repellent composition" refers to a composition comprising a substance which functions as a water repellent agent, and is used for imparting water repellence to an application subject of the composition.

The "composition of the present invention" refers to the "ultraviolet reflecting agent composition of the present invention" and the "water repellent composition of the present invention" collectively.

In one embodiment, the ultraviolet reflecting agent composition of the present invention may be used to impart water repellence to an application subject of the composition.

Additionally, in another embodiment, the water repelling agent composition of the present invention may be used to impart an ultraviolet reflecting property to an application subject of the composition.

In the present description, "ultraviolet light" refers to electromagnetic waves having a wavelength from 100 to 400 nm, and is divided according to wavelength into long-wave ultraviolet light (400 to 315 nm, called "UVA"), medium-wave ultraviolet light (315 to 280 nm, called "UVB"), and short-wave ultraviolet light (280 to 100 nm, called "UVC"). It is known that as the wavelength of ultraviolet light becomes shorter, its effects on the body become more damaging, for example, its cytotoxicity due to peroxidation reactions or genetic damage becomes higher, whereas as the wavelength of ultraviolet light becomes longer, ultraviolet light affects deeper parts of skin. A portion of medium-wave ultraviolet light UVB and short-wave ultraviolet light UVC are absorbed by the ozone layer in the atmosphere, such that the ultraviolet light that reaches the Earth's surface is long-wave ultraviolet light UVA and a small amount of UVB.

The spectral reflectance when the ultraviolet reflecting agent composition of the present invention is applied to a subject is preferably not less than 10%, not less than 20%, not less than 25%, not less than 30%, not less than 35%, not less than 40%, not less than 50%, or not less than 60% for ultraviolet light with wavelengths not more than 400 nm. The spectral reflectance of the present specification is measured using a spectrometer (for example, HR2000+, Ocean Optics, Inc., USA) or a micro-spectrometer (for example, CRAIC Technologies, Inc., USA).

The water contact angle when the water repelling agent composition of the present invention is applied to a subject is preferably not less than 100°, not less than 110°, not less than 120°, not less than 130°, not less than 140°, or not less than 150°. The "water contact angle" of the present specification refers to the angle formed by the contacting portions between a solid surface and a water droplet formed on the solid surface. The water contact angle of the present specification is measured using a contact angle meter (for example, MCA-3: Kyowa Interface Science, Japan).

The composition of the present invention comprises at least one compound selected from 2-pentacosanone, 2-heptacosanone, 2-nonacosanone, tetracosanal, hexacosanal, octacosanal, and triacontanal, preferably comprising at least one compound selected from 2-pentacosanone, 2-heptacosanone, and 2-nonacosanone, or more preferably comprising 2-pentacosanone.

The long-chain aliphatic aldehydes and ketones which the composition of the present invention may comprise may be extracts from natural products, or may be artificially synthesized through a combination of known methods.

In one embodiment, the composition of the present invention comprises an organic solvent extract from a mature white tailed skimmer dragonfly, preferably comprising an organic solvent extract from a mature male white tailed skimmer dragonfly. The organic solvent used may be, for example, hexane or chloroform.

If necessary, the composition of the present invention may, in addition to the long-chain aliphatic aldehydes and ketones which are the active agents, comprise one or more types of additives commonly used in the formulation field (for example, antioxidants, surfactants, thickeners, preservatives, pH adjusters, chelating agents, stabilizers, irritation reducers, preservatives, colorants, fragrances, oils, water, alcohols, silicones, and humectants) to an extent that the efficacy of the present invention is not reduced.

The composition of the present invention is preferably a composition for external use on the skin or a paint composition, or more preferably, a composition for external use on the skin. Additionally, in one embodiment, the composition for external use on the skin is a sunblock composition.

The form of the composition of the present invention is not particularly limited. For example, it may be a liquid, emulsion, gel, paste, or cream. When the composition of the present invention is a cosmetics composition, the form can be, for example, a basic cosmetic such as a lotion, emulsion, cream, essence, sunblock cosmetic, pack, hand cream, body lotion, or body cream; a cleansing cosmetic such as a facial wash, make-up remover, or body wash; or a makeup cosmetic such as a foundation, makeup base, lip cream, lipstick, or blush.

The form of the active agent of the composition of the present invention is not particularly limited, as long as it can impart ultraviolet reflecting property to an application subject of the composition and/or it can impart water repellence to an application subject of the composition. Additionally, the active agent may be crystalline, or may be non-crystalline, or a mixture thereof.

In one embodiment, the active agent of the composition of the present invention has a structure formed by repeatedly dripping a solution of the active agent onto a substrate. The solvent is not particularly limited, but may be, for example, hexane or chloroform. The concentration of the solution is not particularly limited and is, for example, 0.1 to 100 mM, 0.2 to 50 mM, or 0.5 to 10 mM. The drip interval is not particularly limited as long as crystals precipitate out, and is, for example, 60 seconds to 180 seconds. When the solution is dripped on the microcrystals of the active agent, it is preferable that the microcrystals grow before dissolving. The substrate used is not particularly limited, and is, for example, a metal (iron, copper, aluminum, nickel, zinc, stainless steel, or the like), or a glass or plastic plate. The temperature during dripping is, for example, 0° C. to 50° C., or 5° C. to 40° C.

In another embodiment, the active agent of the composition of the present invention has a structure formed by melting and subsequently cooling the active agent. The cooling temperature is not particularly limited, and is, for example −10° C. to less than the melting point of the active agent. The time from the melting temperature to the cooling temperature is not particularly limited, and is, for example, 1 second to 1 hour, 1 second to 30 minutes, or 1 second to 10 minutes.

One aspect of the present invention provides a method for protecting a subject from ultraviolet light, comprising applying at least one compound selected from 2-pentacosanone, 2-heptacosanone, 2-nonacosanone, tetracosanal, hexacosanal, octacosanal, and triacontanal to a subject. Another aspect of the present invention provides a method performing water repellence treatment on a subject, comprising applying at least one compound selected from 2-pentacosanone, 2-heptacosanone, 2-nonacosanone, tetracosanal, hexacosanal, octacosanal, and triacontanal to a subject. Both methods are collectively referred to as the "method of the present invention".

In the present description, the method for "applying" may be any method as long as the method ensures that the application substance adheres to a certain location on the application subject. For example, the substance to be applied on the application subject may be painted or sprayed on the application subject.

The subject to which the composition of the present invention is applied and the subject in the method of the present invention are not particularly limited, and are, for example, any type of material (for example, paper, metal, wood, glass, plastic, concrete, ceramic), or animals (for example, humans). The subject is preferably a human, and more preferably, human skin.

The present invention will be specifically described by way of the Examples. However, the claims of the present invention are not limited thereto.

EXAMPLES

Example 1

Spectral Reflectance Measurement of the Dorsal Side and Ventral Side of the Fifth Segment of the Abdomen of a White Tailed Skimmer Dragonfly The ventral side and dorsal side of the surgically-dissected fifth segment of the abdomen of a white tailed skimmer dragonfly were used for the measurement of spectral reflectance. Spectral reflectance from the small field was measured using a spectrometer (HR2000+, Ocean Optics, Inc., USA). By normalizing the reflected spectral radiation using a white reflection standard (Spectralon USRS-99-010, Labsphere Inc., USA), it was converted to a relative spectral reflectance. The results are shown in FIG. 1. The spectral reflectance was particularly high for the dorsal side of a mature white tailed skimmer dragonfly.

Example 2

Figure 2:
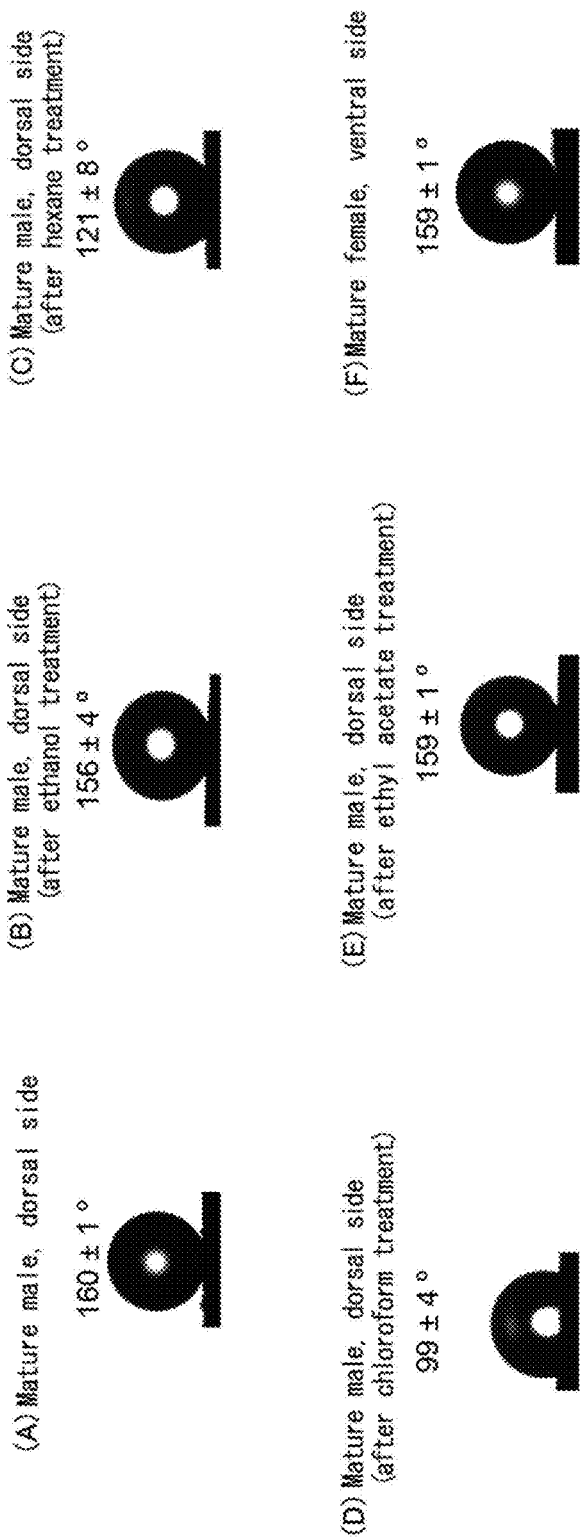
FIG. 2 shows the results of contact angle measurements of the dorsal sides and ventral sides of the fifth segments of the abdomens of white tailed skimmer dragonflies.

Water Contact Angle Measurement of the Dorsal Side and Ventral Side of the Fifth Segment of the Abdomen of a White Tailed Skimmer Dragonfly Water repellence was evaluated based on the contact angle of a tiny droplet of water on the surface of a sample. After each sample was fixed on a glass substrate, tiny water droplets (about 1.0 nL) of distilled water were placed on the surface of the sample. Using a contact angle meter (MCA-3: Kyowa Interface Science, Japan) of a microscope and a high-speed camera HAS-220 (Ditect Japan), the shape of the droplets was recorded immediately. The results are shown in FIG. 2.

The dorsal side of the mature male and the ventral side of the mature female demonstrated high contact angles. The contact angle for the dorsal side of the mature male dropped when treated with organic solvent. In particular, the contact angle particularly dropped for the parts treated with chloroform since all of the wax present on the surface of the parts eluted.

Example 3

Figure 3:
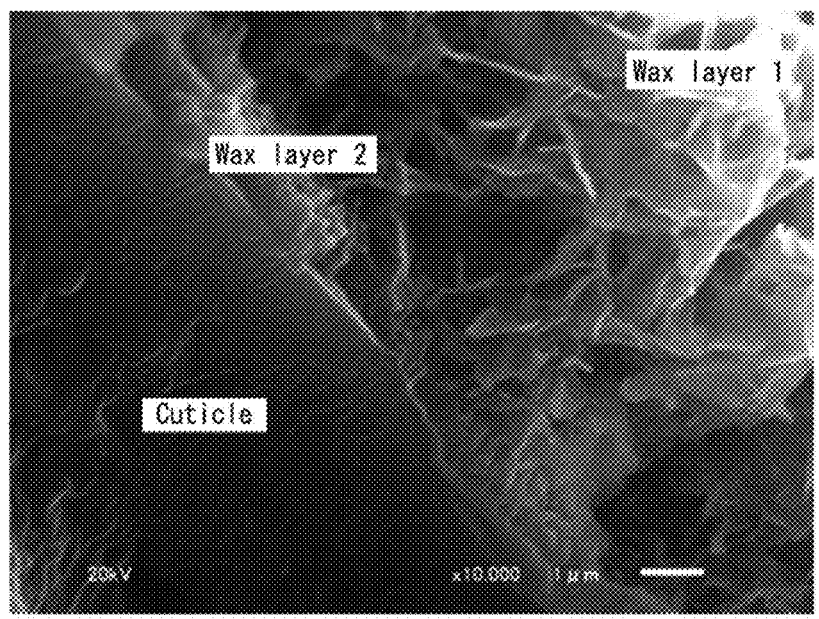
FIG. 3 shows an SEM image of the dorsal side of the fifth segment of the abdomen of a male white tailed skimmer dragonfly.

Scanning Electron Microscope (SEM) Observation of the Dorsal Side of the Fifth Segment of the Abdomen of a Male White Tailed Skimmer Dragonfly An S5 fragment was dissected from a white tailed skimmer dragonfly, and further divided into a ventral side and a dorsal side. In order to maintain wax on the surface, solution treatment was omitted, and the dorsal side was placed on carbon tape adhered to an aluminum test material table, and coated with a 2 to 3 nm osmium film using a hollow cathode plasma CVD (HPC-1SW, Vacuum Device Inc., Japan). Observation was performed using a Hitachi H-4800 scanning electron microscope at an acceleration voltage of 5 kV. The results are shown in FIG. 3. In FIG. 3, Wax 1 represents a layer soluble in hexane. Wax 2 represents a layer poorly soluble in hexane, but soluble in chloroform.

Example 4

Figure 5:
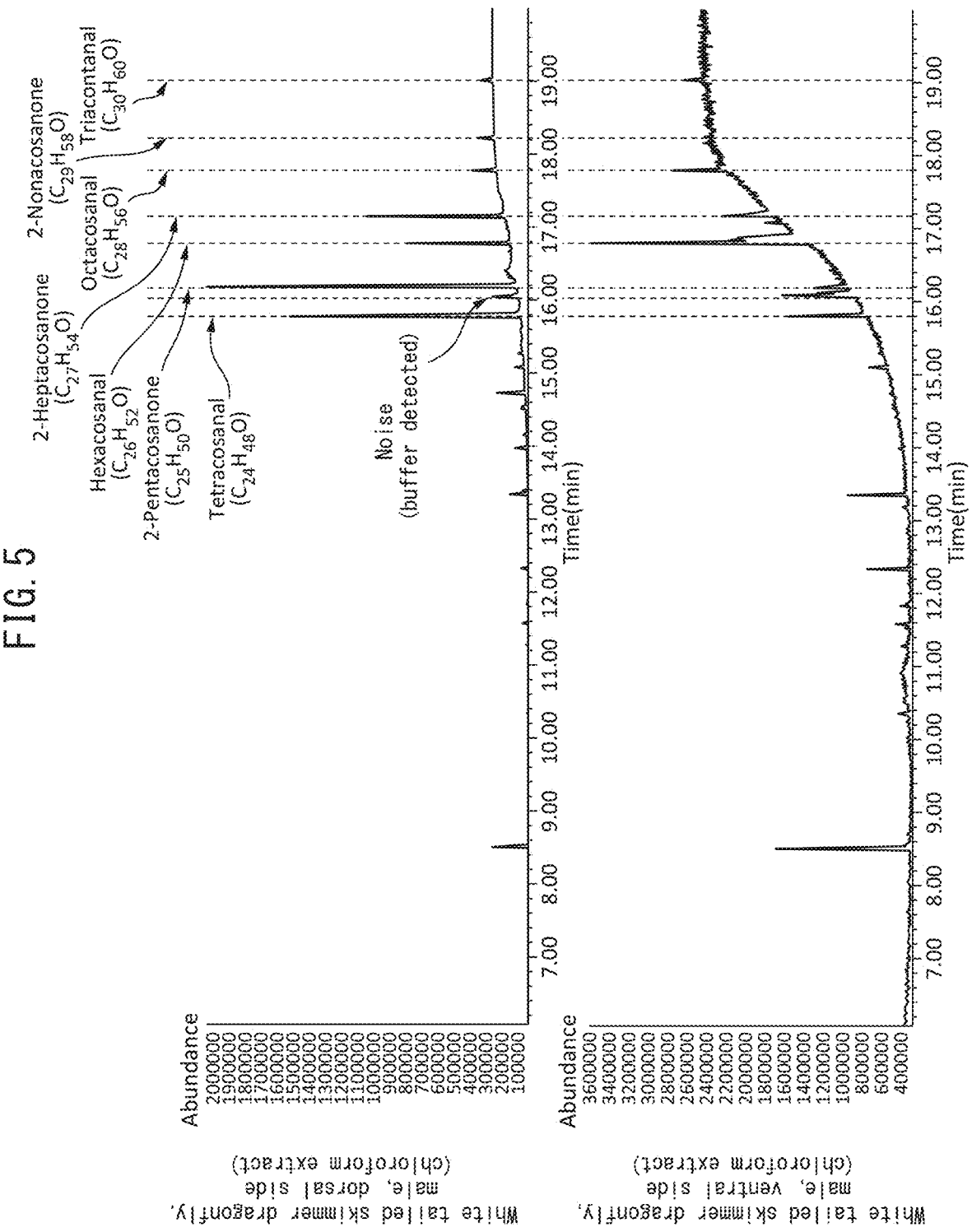
FIG. 5 shows TIC as measured by GC-MS of extracts taken from the dorsal side and ventral side of the fifth segment of the abdomen of a male white tailed skimmer dragonfly using chloroform.
Figure 6:
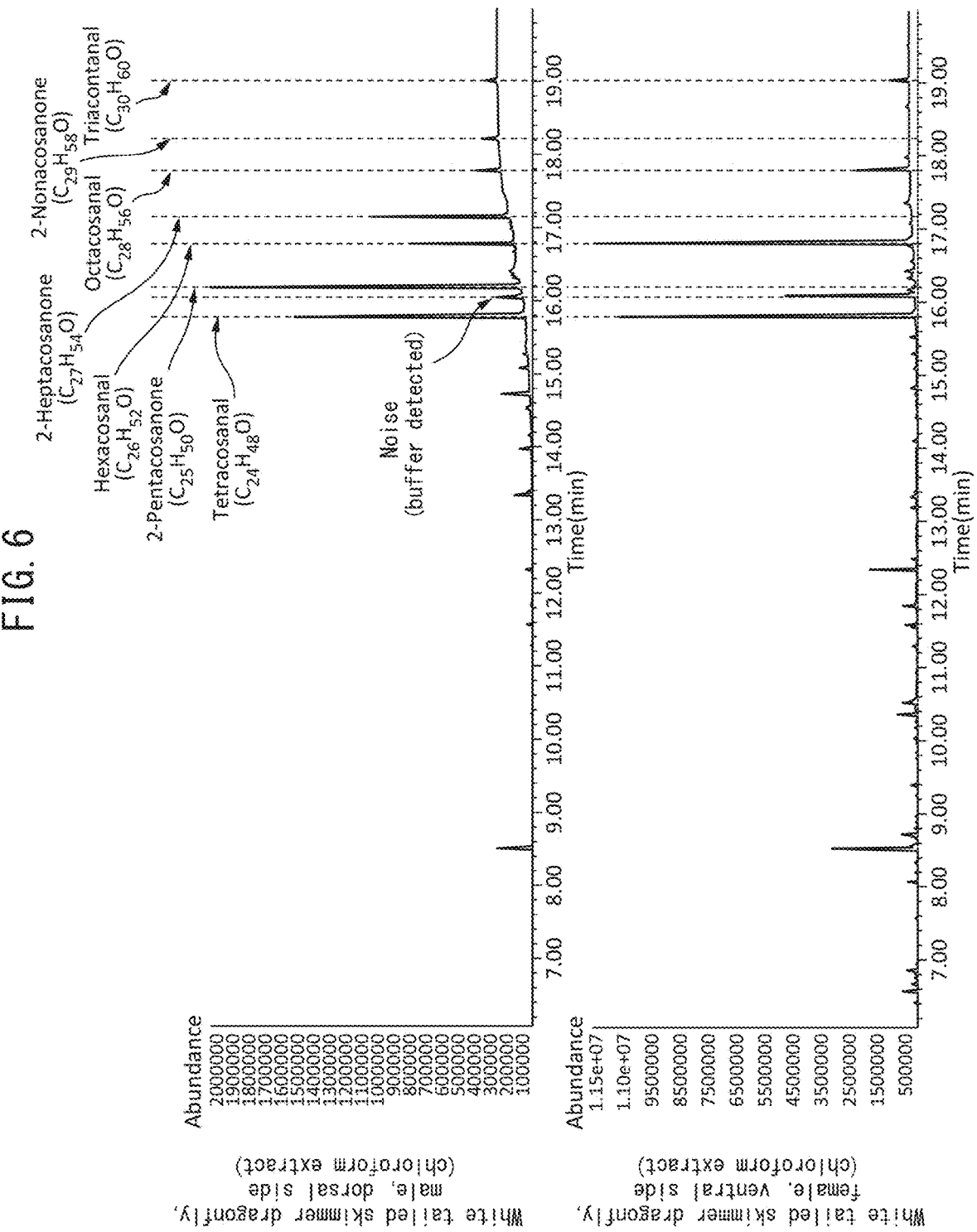
FIG. 6 shows TIC as measured by GC-MS of extracts taken from the dorsal side of the fifth segment of the abdomen of a male white tailed skimmer dragonfly and the ventral side of the fifth segment of the abdomen of a female white tailed skimmer dragonfly using chloroform.

GC-MS Analysis of Organic Solvent Extract of the Fifth Segment of the Abdomen of a White Tailed Skimmer Dragonfly Using a 6890N GC and 5973inert MS from Agilent Technologies (Palo Alto, Calif.), GC-MS analysis was performed on the organic solvent extract from the fifth segment of the abdomen of a white tailed skimmer dragonfly. The injection temperature was set to 250° C. The injection was performed in splitless mode. Separation was performed using a DB-5MS fused silica column (30 μm×0.25 mm inner diameter, 0.25 μm film thickness, Agilent Technologies). The oven temperature was programmed to rise from 80° C. (maintained for 1 minute) to 320° C. (maintained for 3 minutes) at a rate of 15° C./minute. Helium was used as a carrier gas at a flow rate of 1.0 mL/minute. The mass spectrometer was operated in a scan mode with electron ionization (EI). The ionization voltage was set to 70 eV. Regarding the scan mode, ion radius was set from m/z 20 to 600. The results are shown in FIGS. 4 to 6.

Figure 4:
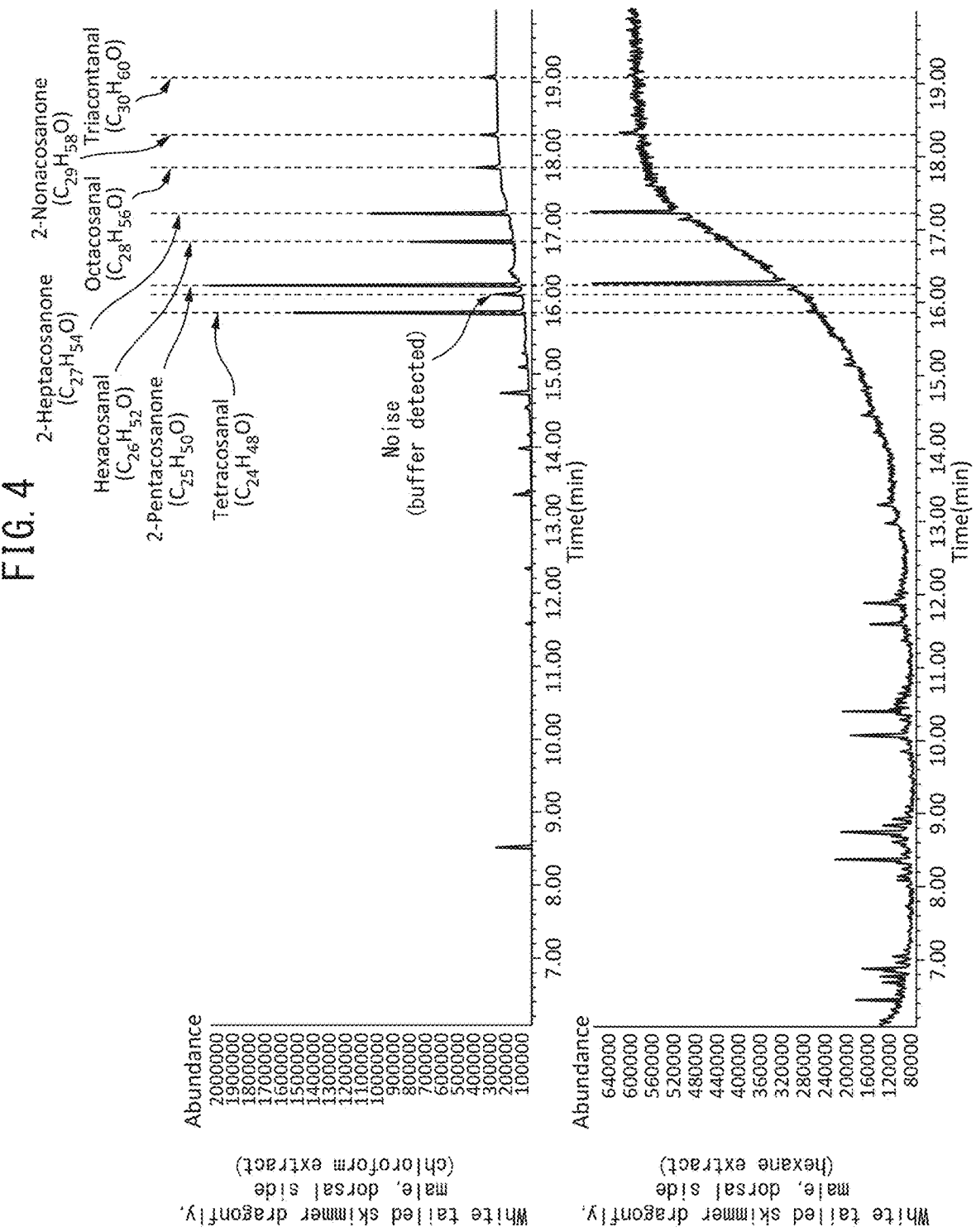
FIG. 4 shows total ion chromatograms (TIC) as measured by GC-MS of extracts taken from the dorsal side of the fifth segment of the abdomen of a male white tailed skimmer dragonfly using chloroform or hexane.

It became clear that the dorsal side of the male white tailed skimmer dragonfly, which demonstrated high spectral reflectance, contained 2-pentacosanone, 2-heptacosanone, and 2-nonacosanone, which are long-chain aliphatic ketones, and tetracosanal, hexacosanal, octacosanal, and triacontanal, which are long-chain aliphatic aldehydes (FIG. 4). The above ketones and aldehydes were detected on the ventral side of the male white tailed skimmer dragonfly, but the ratio of ketones to the total amount of extract was lower on the ventral side than on the dorsal side (FIG. 5). For the ventral side of a female white tailed skimmer dragonfly, the ketones were minimally detected, but the long-chain aliphatic aldehydes of tetracosanal, hexacosanal, octacosanal, and triacontanal were primarily detected (FIG. 6). For the dorsal side of a female white tailed skimmer dragonfly, neither long-chain aliphatic ketones nor long-chain aliphatic aldehydes were detected.

Example 5

Synthesis and Physical Properties of 2-Pentacosanone (1) Synthesis of 1-Tetracosanal Pyridinium chlorochromate (PCC) (1.29 g, 5.97 mmol) was added to a suspension of 1-tetracosanal (395 mg, 1.11 mmol) and a powdered molecular sieve 4A (2.5 g) in dried $CH_2Cl_2$ (35 mL). The reaction mixture was stirred for 4 hours at room temperature. The mixture was celite filtered, and washed with diethyl ether. The filtrate and washings were filtered through florisil (15 g), washed with diethyl ether (200 mL), and concentrated under reduced pressure. The residue underwent silica gel chromatography (silica gel 15 g), was concentrated under reduced pressure, and the subject substance was acquired as a white solid (290 mg, 0.82 mmol, 74%).

GC $t_R$=23.7 minutes, MS m/z (%): 352 (M*, 2), 334 (18), 96 (78), 82 (100), 57 (93), 43 (72).

(2) Synthesis of 2-Pentacosanol

A dried THF (10 mL) solution of the 1-tetracosanal (176 mg, 0.50 mmol) obtained in (1) was cooled in an ice bath. After the temperature reached 0° C., a THF/toluene (1:3) mixed solution (1 mL, 1.4 mmol) of 1.4 M $CH_3MgBr$ was dripped thereinto. The solution was stirred for 1.5 hours at 0° C. The reaction was quenched with a saturated $NH_4Cl$ (5 mL) solution. Products were extracted using hexane (3×20 mL). The organic layer was dried with anhydrous magnesium sulfate and concentrated under reduced pressure. The residue underwent silica gel chromatography (silica gel 15 g, ethyl acetate:hexane=1:5), and the subject substance was obtained as a white solid (106 mg, 0.29 mmol, 58%).

$^1$H-NMR ($CDCl_3$, 400 MHz): δ 3.79 (1H, sex, J=6.0 Hz, H–2), δ 1.18 (3H, d, J=6.0 Hz, H–1), δ0.88 (3H, t, J=6.0 Hz, H–25).

(3) Synthesis of 2-Pentacosanone

PCC (335 mg, 1.56 mmol) was added to a suspension of the 2-pentacosanol (257 mg, 0.70 mmol) obtained in (2) and a powdered molecular sieve 4A (1.0 g) in dried $CH_2Cl_2$ (20 mL). The reaction mixture was stirred for 3 hours at room temperature. The mixture was celite filtered, and washed in diethyl ether. The filtrate and the washings were filtered through florisil (15 g), washed in diethyl ether (200 mL), and concentrated under reduced pressure. The residue was recrystallized from hexane and the subject substance was acquired as a white solid (referred to as "Crystal 1") (202 mg, 0.55 mmol, 76%).

$^1$ H-NMR ($CDCl_3$, 400 MHz): δ 2.41 (2H, d, J=7.6 Hz, H-3), δ 2.13 (3H, s, H-1), δ 0.88 (3H, t, J=6.4 Hz, H-25). GC $t_R$=24.3 min, MS m/z (%): 366 (M+, 21), 351 (8), 306 (7), 207 (8), 71 (55), 59 (100), 43 (66).

Melting point: about 77° C.

Figure 7:
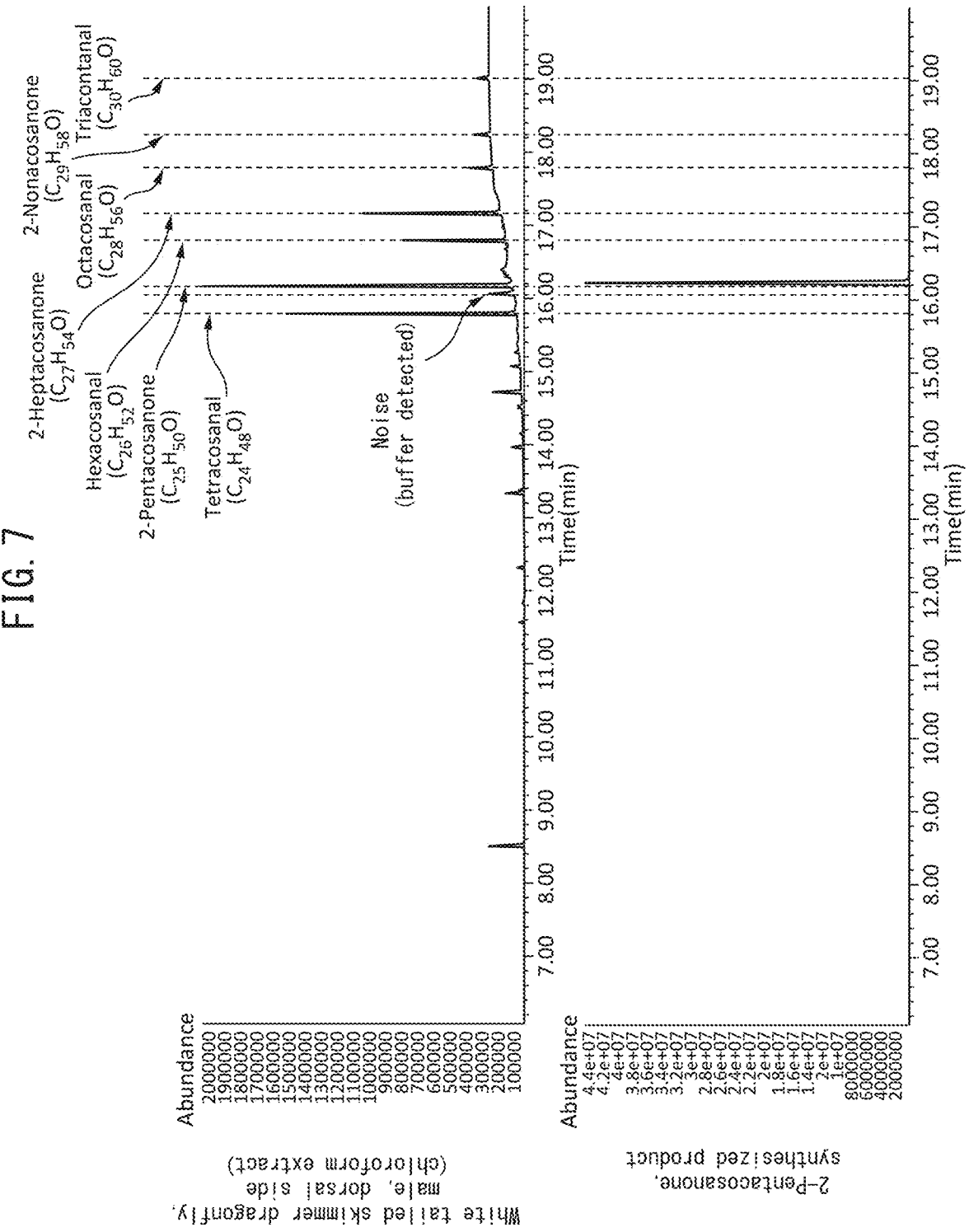
FIG. 7 shows TIC as measured by GC-MS of 2-pentacosanone synthesized in Example 5 and an extract taken from the dorsal side of the fifth segment of the abdomen of a male white tailed skimmer dragonfly using chloroform.

The TIC of Crystal 1 of 2-pentacosanone as measured by GC-MS is shown in FIG. 7.

(4) Evaluation using 2-pentacosanone crystals having different surface structures A 1 mM/L hexane solution (1 μL) of the 2-pentacosanone obtained in Example 5 (3) was dripped onto a glass substrate. After drying, another 1 μL was dripped. This process was repeated five times (time interval between one drop and the next drop: 120 seconds) and a crystal was obtained. The crystal obtained is referred to as "Crystal 2".

The 2-pentacosanone (1 mg) obtained in Example 5 (3) was placed on a glass substrate, heated to 80° C., melted, and thereafter, placed together with the glass substrate on a 0° C. cooling plate to cool. The crystal grew instantly. The crystal obtained is referred to as "Crystal 3".

The 2-pentacosanone (1 mg) obtained in Example 5 (3) was placed on a glass substrate, heated to 80° C., melted, and thereafter, placed together with the glass substrate on a 76° C. hot plate for 3 minutes and then slowly cooled, whereby a crystal grew. The crystal obtained is referred to as "Crystal 4".

Figure 8:
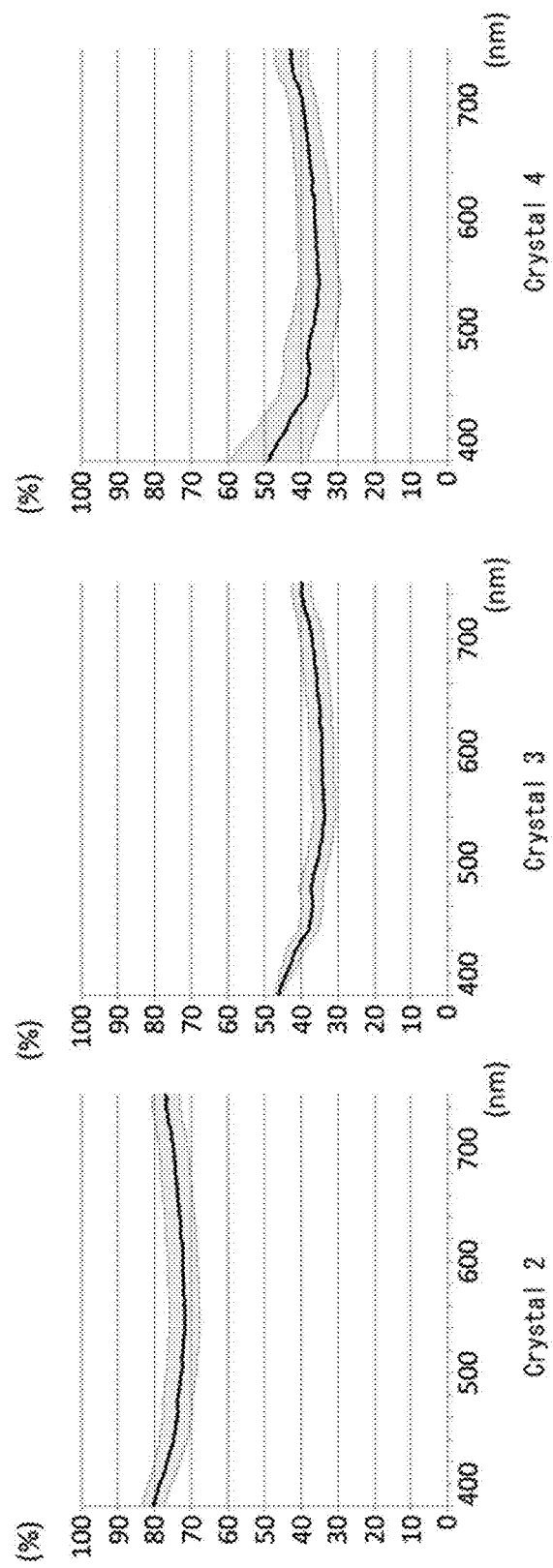
FIG. 8 shows spectral distributions for Crystals 2 to 4 of 2-pentacosanone synthesized in Example 5 (4).
Figure 9:
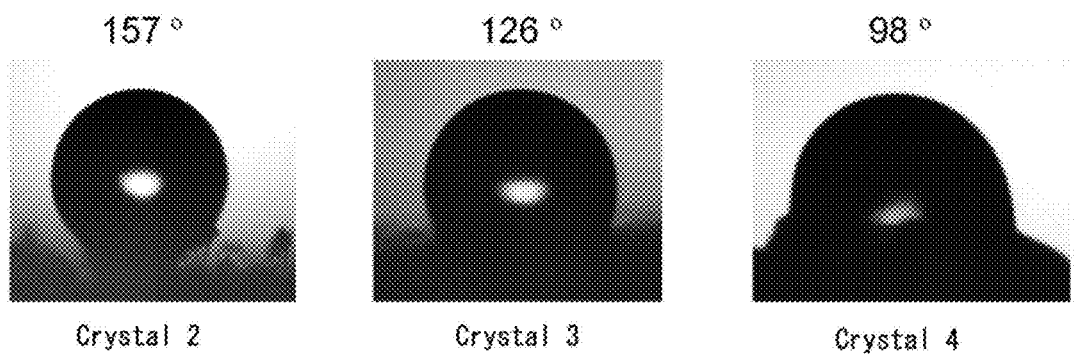
FIG. 9 shows the contact angles measurements for Crystals 2 to 4 of 2-pentacosanone synthesized in Example 5 (4).

The spectral reflectivities of Crystals 2 to 4 were measured using a microspectrophotometer (CRAIC Technologies, Inc., USA) comprising an upright microscope (Nikon Eclipse E-400, Nikon Co. Ltd., Japan). The measurement results were obtained by irradiating a sample using a 75 W xenon arc lamp (Nikon Co. Ltd., Japan). By normalizing the reflected spectral radiation using a white reflection standard (Spectralon USRS-99-010, Labsphere Inc., USA), it was converted to a relative spectral reflectivity. The results for spectral distributions of Crystals 2 to 4 are shown in FIG. 8. Crystal 2 demonstrated a particularly high ultraviolet light reflectance. Additionally, the results for contact angle measurements of Crystals 2 to 4 are shown in FIG. 9. Crystal 2 demonstrated particularly high water repellence.

Figure 10:
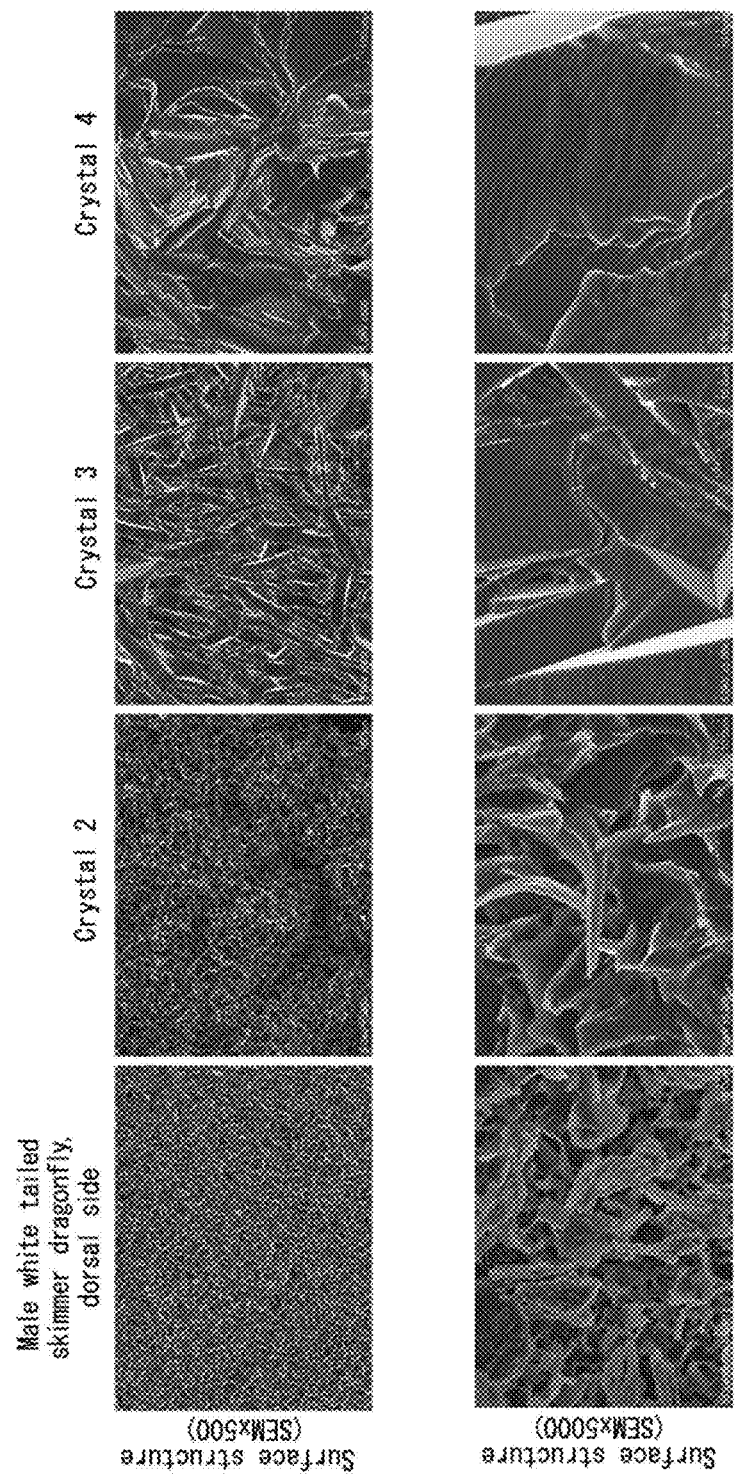
FIG. 10 shows SEM images (magnification of upper images is 500 and magnification of lower image is 5000) of Crystals 2 to 4 of 2-pentacosanone synthesized in Example 5 (4). SEM images of the surface of the dorsal side of the fifth segment of the abdomen of a male white tailed skimmer dragonfly are shown for the sake of comparison.

SEM images of the surface structures of Crystals 2 to 4 are shown in FIG. 10. For comparison, SEM images of the surface structure of the dorsal side of a mature male white tailed skimmer dragonfly are likewise shown. The surface structure of Crystal 2 resembles the surface structure of the dorsal side of a mature male white tailed skimmer dragonfly.

Example 6

Genetic Analysis

Figure 11:
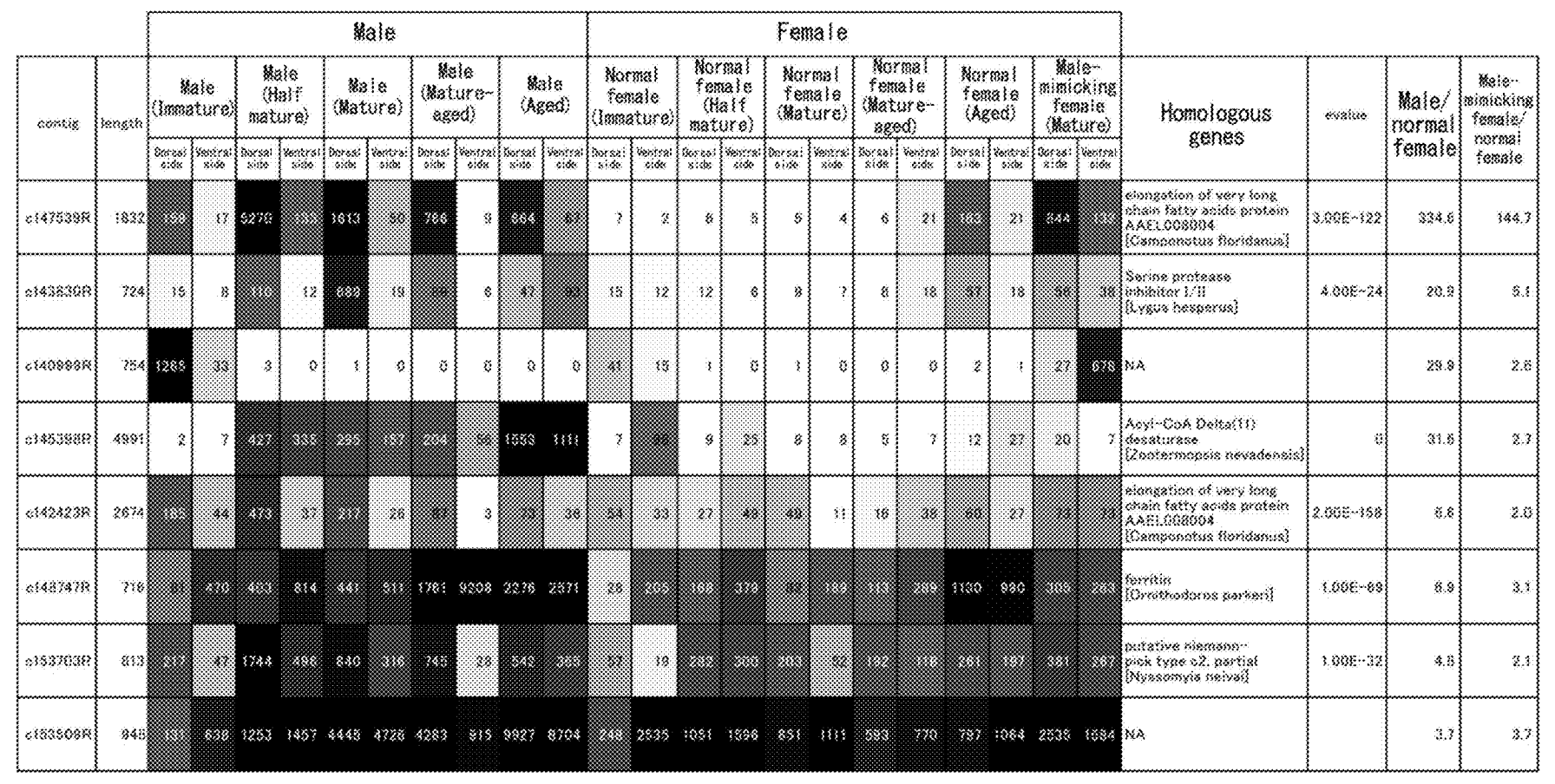

A total RNA sample was extracted from the dissected ventral of a fresh white tailed skimmer dragonfly using an RNeasy mini kit (Qiagen) or a Maxwell 16 LEV Simply RNA Tissue kit (Promega). Using TruSeq RNA Sample Preparation Kits v2 (Illumina), a cDNA library was constructed using 1 μg of total RNA per sample, and sequencing was performed by HiSeq2000, Hiseq2500, or MiSeq (Illumina). De novo assembly of the raw lead was performed using the Trinity program (Grabherr, M. G. et al., "Full-length transcriptome assembly from RNA-Seq data without a reference genome", Nat. Biotechnol. 29, pp. 644-52 (2011)) executed in the MASER pipeline (http://cell-innovation.nig.ac.jp/). After automatic assembly, the sequences highly expressed in a mature male were confirmed using an Integrative Genomics Viewer (Thorvaldsdottir H, Robinson J T, Mesirov J P (2013), "Integrative Genomics Viewer (IGV): high-performance genomics data visualization and exploration", Brief Bioinform. 14: pp. 178-192), and were manually revised. After revising the sequence, lead matching was performed using the BWA-MEM program (Li, H., (2013) "Aligning sequence reads, clone sequences and assembly contigs with BWA-MEM", arXiv: 1303. 3997 [q-bio.GN]) executed in the MASER pipeline, and the expression level of transcription products was estimated as a fragments per kilobase per million reads (FPKM) value thereby. The results are shown in FIG. 11. As a result of analysis, a gene which was expressed 335 times more in the dorsal side of a male than in the dorsal side of a normal female (excluding aged individuals) and 145 times more in the dorsal side of a male-mimicking female than in the dorsal side of a normal female was discovered (FIG. 11, c147539R). It is considered that the gene (sequence number 1) is related to the synthesis of long-chain aliphatic ketones specific to the dorsal side of a male.

INDUSTRIAL APPLICABILITY

The composition of the present invention has an ultraviolet reflecting effect and a water repellent effect, and can be suitably used in cosmetics and paints.

Sequence Listing Free Text

The invention claimed is:

1. A method for protecting a subject from ultraviolet rays comprising applying at least one compound selected from 2-pentacosanone, 2-heptacosanone, 2-nonacosanone, tetracosanal, hexacosanal, octacosanal, and triacontanal to the subject.

2. The method according to claim 1, wherein, when the compound is applied to a subject, the surface structure has a spectral reflectance of not less than 30% for UV light with a wavelength 400 nm or less.

3. The method according to claim 1, wherein the compound is 2-pentacosanone.

4. The method according to claim 1, wherein the compound is in crystalline form having a structure formed by repeatedly dripping a solution of the compound onto a substrate.

5. The method according to claim 1, wherein the subject is an animal.

6. The method according to claim 1, wherein the subject is human skin.

7. The method according to claim 1, wherein the subject is a material selected from paper, metal, wood, glass, plastic, concrete or ceramic.

8. A method for water-repellent treatment of a subject comprising applying at least one compound selected from 2-pentacosanone, 2-heptacosanone, 2-nonacosanone, tetracosanal, hexacosanal, octacosanal, and triacontanal to the subject.

9. The method according to claim 8, wherein, when the compound is applied to a subject, the surface structure wherein the water contact angle is not less than 150° is formed.

10. The method according to claim 8, wherein the compound is 2-pentacosanone.

11. The method according to claim 8, wherein the compound is in crystalline form having a structure formed by repeatedly dripping a solution of the compound onto a substrate.

12. The method according to claim 8, wherein the subject is an animal.

13. The method according to claim 8, wherein the subject is human skin.

14. The method according to claim 8, wherein the subject is a material selected from paper, metal, wood, glass, plastic, concrete or ceramic.

15. A method of producing an ultraviolet reflecting agent composition comprising the step of repeatedly dripping a solution of at least one compound selected from 2-pentacosanone, 2-heptacosanone, 2-nonacosanone, tetracosanal, hexacosanal, octacosanal, and triacontanal onto a substrate to form a crystalline form thereof, wherein the ultraviolet reflecting agent comprises the crystalline form as an active agent.

16. The method according to claim 15, wherein, when the ultraviolet reflecting agent composition is applied to a subject, the surface structure wherein the spectral reflectance for UV light with a wavelength 400 nm or less is not less than 30% is formed.

17. The method according to claim 15, wherein the compound is 2-pentacosanone.

18. The method according to claim 15, wherein the ultraviolet reflecting agent composition is a cosmetic.

19. The method according to claim 15, wherein the ultraviolet reflecting agent composition is a paint.

20. A method of producing a water repellent composition comprising the step of repeatedly dripping a solution of at least one compound selected from 2-pentacosanone, 2-heptacosanone, 2-nonacosanone, tetracosanal, hexacosanal, octacosanal, and triacontanal onto a substrate to form a crystalline form thereof, wherein the water repellent composition comprises the crystalline form as an active agent.

21. The method according to claim 20, wherein, when the water repellent composition is applied to a subject, the surface structure wherein the water contact angle is not less than 150° is formed.

22. The method according to claim 20, wherein the compound is 2-pentacosanone.

23. The method according to claim 20, wherein the water repellent composition is a cosmetic.

24. The method according to claim 20, wherein the water repellent composition is a paint.

* * * * *

SEQUENCE LISTING

```
<160> NUMBER OF SEQ ID NOS: 1

<210> SEQ ID NO 1
<211> LENGTH: 1832
<212> TYPE: DNA
<213> ORGANISM: Orthetrum albistylum speciosum

<400> SEQUENCE: 1
gcgcgcaacc atggccacca acatggctgc ggggatcctc cgtggatacc gggacctcat      60
ggacaaccag agcgatgaga gagtgaagaa ttggttcctg atgggaagtc ctttccccac     120
ccttttcatg tgcctcacat acgtgtggat cgtgaaatat gccggaccaa agttcatgga     180
gaagagaaag ccctatgatc tccgcagatt ccttttcttc tacaacattt tccaagtgtc     240
ttacaatggc tggctttttct acgagggcgt ttcgcggtgg tttggacgga actacagctt     300
cagatgccaa ccagtagatt acagttacaa tccagaggct gtcagggtgg ccgaactatg     360
ctggtggtac tacatctgca aacttaccga gttcacagat acgttttcgt tcgtgttgag     420
gaagaagaac gaccacataa gcaatctgca tgtgattcac catggagtta tgccactcag     480
tgtgtggttt ggagtgaagt tcactccagg cggccacagc actttcttcg gcatcttgaa     540
tacaggagtt cacgtgatca tgtattctta ctatttgctg gcaacacttg gaccaaatat     600
gaagaggtac ttgtggtgga agagacatgt cacttcacta caaatgattc atttcgtggt     660
cataatgctc cattcctttc aactgctgtt ccacgagggc tgcgactacc ccaagttctt     720
catctggtgg atcggattac atgccgtcat gttctacttg ttcttcactg aattctacaa     780
gcagcaatat ggcagaagtc cgcctctgaa cgcaatattt gaaaagaaaa tgaactgaag     840
ctctgcacac gtggaattcg cagaatcaag cagatgatct tttgccaaca acgtcgcttc     900
tcagctgtta acttcccact gtaaaccccc cagcagagac agatttatta tactttcatc     960
aattcactca ataaccagta ttgatttaga tttagagctg ctccgtcaaa gtgaggggaa    1020
cgggcggcgg atagctttcc atccagtatt tgaagaaatg agggagattt tgagaccact    1080
cggtgctccc atacacacta cactgatacg tgtatcaatt catatctgcg aacaattaaa    1140
tgaacatctt ccgtggctaa tatgaacaga atttacagtc caatacgtca ttgttaatta    1200
ctaaaacttg aaatttcgag acagcgaaag cgctcatttt ggccaaatcg tcatcttcag    1260
atcgtaaata atagtttgac tggagccgaa aggaaggaga cgtcttgaga cgagaaccag    1320
gtcacgcctg acgcgtgata agtgacacaa tattgatttc gccatcatta cttcaatcct    1380
acgttgaatc atcttctcgt ttggaccgga agaacctcgc tccggtctag catagcaacc    1440
accatttgaa actcacccca ggaaactggt ttctcgggat gaaccggacc cataggaatc    1500
ccatgtttgg ctgtgtgacc catttccacg ctctctctct ccgattccgc tacgcattct    1560
```

```
gggcgagcac aagttcgtct aaaggagatg atttttactc tcaattgttt tcgctttatt    1620
gattaatttt cagacggcga aacacttccg ttgttgtttt atattctggg taaaatgaaa    1680
ggatgataaa gaataaggac attttctatc gcattgcagt gaactgaaga gcgaaaggtg    1740
ttggaaacgc caaggcccag tgttttttt tatagctgat gttgtattaa ctttaagttg    1800
ttgaaataaa tttatgaata aatagatacc aa                                 1832
```